United States Patent
Lee et al.

(10) Patent No.: US 10,501,745 B2
(45) Date of Patent: Dec. 10, 2019

(54) PROMOTER AND USE THEREOF

(71) Applicant: CJ CHEILJEDANG CORPORATION, Seoul (KR)

(72) Inventors: Young Mi Lee, Bucheon-si (KR); Seung Bin Lee, Suwon-si (KR); Seong Bo Kim, Seoul (KR); Ji Hyun Lee, Suwon-si (KR); Jin Sook Chang, Suwon-si (KR); Seung Hyun Cho, Seoul (KR); Seung Won Park, Yongin-si (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 17 days.

(21) Appl. No.: 15/563,750

(22) PCT Filed: Mar. 11, 2016

(86) PCT No.: PCT/KR2016/002481
§ 371 (c)(1),
(2) Date: Oct. 2, 2017

(87) PCT Pub. No.: WO2016/159536
PCT Pub. Date: Oct. 6, 2016

(65) Prior Publication Data
US 2018/0094268 A1    Apr. 5, 2018

(30) Foreign Application Priority Data
Apr. 2, 2015 (KR) .................. 10-2015-0047111

(51) Int. Cl.
| | |
|---|---|
| *A01N 63/00* | (2006.01) |
| *C07H 21/04* | (2006.01) |
| *C12N 15/00* | (2006.01) |
| *C12P 21/06* | (2006.01) |
| *C12N 15/70* | (2006.01) |
| *C12R 1/19* | (2006.01) |
| *C12P 19/02* | (2006.01) |
| *C12P 21/00* | (2006.01) |
| *C12N 15/63* | (2006.01) |
| *C12R 1/15* | (2006.01) |
| *C12P 21/02* | (2006.01) |
| *C12N 15/77* | (2006.01) |
| *C12N 15/74* | (2006.01) |

(52) U.S. Cl.
CPC ............. *C12N 15/70* (2013.01); *C12N 15/63* (2013.01); *C12N 15/77* (2013.01); *C12P 19/02* (2013.01); *C12P 21/00* (2013.01); *C12P 21/02* (2013.01); *C12R 1/15* (2013.01); *C12R 1/19* (2013.01); *C07H 21/04* (2013.01); *C12N 15/74* (2013.01)

(58) Field of Classification Search
CPC ........ C12N 15/63; C12N 15/74; C12N 15/77; C12N 2510/00; C07H 21/04; C12P 19/02; C12P 21/02
USPC ............ 435/320.1, 69.1; 424/93.2; 536/23.2, 536/24.1
See application file for complete search history.

(56) References Cited

U.S. PATENT DOCUMENTS

| | | | |
|---|---|---|---|
| 7,785,779 B2 † | 8/2010 | Kroger | |
| 8,426,195 B2 † | 4/2013 | Rah | |
| 8,426,577 B2 * | 4/2013 | Kim .................... | C12N 9/0008 435/115 |
| 2008/0138859 A1 † | 6/2008 | Park | |

FOREIGN PATENT DOCUMENTS

| | | |
|---|---|---|
| KR | 10-06200920000 B1 | 8/2006 |
| KR | 10-09240650000 B1 | 10/2009 |
| KR | 10-20110035805 A | 4/2011 |
| KR | 10-12038560000 B1 | 11/2012 |
| KR | 10-20140110134 A | 9/2014 |
| KR | 10-20140140215 A | 12/2014 |
| WO | 2015/032761 A1 † | 3/2015 |

OTHER PUBLICATIONS

Follettie et al., 1993, GenEmbl Accession No. L16848, computer printout, pp. 5-6.*
Kim et al., 2010, U.S. Appl. No. 12/864,731 (U.S. Pat. No. 8,426,577), SEQ ID No. 2, computer printout, pp. 3-4.*
Kroger et al., 2006, U.S. Appl. No. 10/582,918 (U.S. Pat. No. 7,785,779), SEQ ID No. 36, computer printout, pp. 7-8.*
Bradford, "A Rapid and Sensitive Method for the Quantitation of Microgram Quantities of Protein Utilizing the Principle of Protein-Dye Binding," *Analytical Biochemistry* 72:248-254 (1976).
Gory et al., "Use of green fluorescent protein to monitor *Lactobacillus sakei* in fermented meat products," *FEMS Microbiology Letters* 194:127-133 (2001).
GenBank: CP010451.1 "Corynebacterium glutamicum strain B253, complete genome," (593 pages) (2015).
Yim et al., "Isolation of fully synthetic promoters for high-level gene expression in Corynebacterium glutamicum," Biotechnol Bioeng. 110(11): 2959-69 (Jun. 2013).†

* cited by examiner
† cited by third party

*Primary Examiner* — Shin Lin Chen
(74) *Attorney, Agent, or Firm* — Seed IP Law Group LLP (57) ABSTRACT

The present disclosure relates to a novel promoter, a vector comprising the promoter, a microorganism comprising the vector, and a method for producing a target protein using the promoter.

17 Claims, 3 Drawing Sheets
Specification includes a Sequence Listing.

PROMOTER AND USE THEREOF

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200187_432USPC_SEQUENCE_LISTING.txt. The text file is 32.2 KB, was created on Sep. 29, 2017, and is being submitted electronically via EFS-Web.

TECHNICAL FIELD

The present disclosure relates to a novel promoter, a vector containing the same, a microorganism containing the vector, and a method for producing a target protein using the promoter.

BACKGROUND ART

In a microorganism of the genus *Corynebacterium* used as a strain for producing amino acids or useful materials which can be used for various purposes such as feeds, medicines, foods, etc., efforts have been continued to increase the production by manipulating the genes in a biosynthetic pathway and/or introduction of a foreign gene, etc. (Korean Patent No. 10-0924065). Inducing the overexpression of a target gene in a microorganism of the genus *Corynebacterium* requires a highly efficient gene expression system. Among these efforts, the selection of a promoter, which is a factor most significantly involved in gene expression, is thus extremely important in a gene expression system. Until now, several promoters derived from *E. coli* (Plac, Ptrc, Ptac) and several promoters derived from microorganisms of the genus *Corynebacterium* (Psod, Peftu, PgapA) have been used as the promoters usable in the microorganisms of the genus *Corynebacterium*. However, the gene expression systems in the microorganisms of the genus *Corynebacterium* showed lower expression efficiency compared to most gene expression systems in *E. coli*.

In this regard, there is a need for the development of a promoter which can exhibit high expression efficiency in the gene expression system of a microorganism of the genus *Corynebacterium*.

DISCLOSURE

Technical Problem

The inventors of the present disclosure have made many efforts to discover a promoter capable of inducing strong gene expression in a strain of the genus *Corynebacterium*, and as a result, have developed a novel promoter and confirmed its high activity, thereby completing the present disclosure.

Technical Solution

An object of the present disclosure is to provide a novel nucleic acid molecule having a promoter activity.

Another object of the present disclosure is to provide a target protein expression cassette which includes the nucleic acid molecule having a promoter activity and a gene encoding a target protein.

Still another object of the present disclosure is to provide a recombinant vector which includes the nucleic acid molecule having a promoter activity.

Still another object of the present disclosure is to provide a recombinant microorganism introduced with the vector.

Still another object of the present disclosure is to provide a method for producing a target protein using the recombinant microorganism introduced with the vector.

Still another object of the present disclosure is to provide a method for producing psicose, which includes: (a) culturing the microorganism introduced with the vector; and (b) reacting the cultured microorganism with fructose to produce psicose.

Advantageous Effects of the Invention

The promoter obtained through the present disclosure exhibits a significantly increased gene expression rate compared to the promoters used in large-scale production of proteins in the existing recombinant microorganisms, and thus, the promoter may be effectively used in foods, pharmaceutical and agricultural industries, etc., where functional materials are to be produced in high yield using the microorganism of the genus *Corynebacterium* or genus *Escherichia* as an expression host.

BEST MODE

In order to achieve the above object, an aspect of the present disclosure provides a nucleic acid molecule having a promoter activity. Specifically, the nucleic acid molecule having a promoter activity may be a nucleic acid molecule having the nucleotide sequence of SEQ ID NO: 1. In the present disclosure, the nucleic acid molecule having the nucleotide sequence of SEQ ID NO: 1 with a promoter activity may be interchangeably used with "spl1 promoter" or "Pspl1".

Additionally, the nucleic acid molecule having a promoter activity may be named as a promoter and all of the terms described above may be used in the present specification.

The promoter of the present disclosure may enable the expression of a target gene, which is operably linked to the nucleic acid molecule having a promoter activity, in a target microorganism and may have the nucleotide sequence of SEQ ID NO: 1, but is not limited thereto.

Additionally, the promoter sequence of the present disclosure may be easily modified by one of ordinary skill in the art by a conventionally-known mutagenesis, such as directional evolution, site-specific mutagenesis, etc. Accordingly, the promoter may include without limitation any nucleotide sequence which shows a homology of 70% or higher, specifically 80% or higher, more specifically 90% or higher, even more specifically 95% or higher, yet even more specifically 98% or higher, and yet even still more specifically 99% or higher, to the nucleotide sequence of SEQ ID NO: 1. Additionally, it should be understood that any nucleotide sequence with a promoter activity having such a homology should also belong to the scope of the present disclosure, even if the nucleotide sequence may have deletion, modification, substitution, or addition, in part of the sequence.

As used herein, the term "homology" refers to a percentage of identity between two polynucleotide or polypeptide moieties. Sequence correspondence from one moiety to another may be determined by a known technique in the art. For example, the homology may be determined by directly aligning the sequence information of two polynucleotide molecules or two polypeptide molecules using a computer program that is readily available and capable of aligning sequence information (e.g., parameters such as score, identity, similarity, etc.), (e.g., BLAST 2.0). Additionally, the homology between polynucleotides may be determined by hybridizing the polynucleotides under a condition for forming a stable double-strand in the homologous regions followed by digesting the hybridized strand by a single-strand-specific nuclease to determine the size of digested fragments.

As used herein, the term "promoter" refers to an untranslated nucleic acid sequence located upstream of a coding region, which includes a polymerase-binding site and has the activity of initiating transcription of a gene located downstream of a promoter into mRNA, i.e., a DNA domain to which polymerase binds and initiates the transcription of a gene. The promoter may be located at the 5' domain of mRNA transcription initiation region.

The nucleic acid molecule of a promoter of the present disclosure may be isolated or prepared using the standard molecular biology technology. For example, the nucleic acid molecule of a promoter may be prepared using a standard synthesizer technology which uses an automated DNA synthesizer, but is not limited thereto.

Although the type of cell in which the nucleic acid molecule having a promoter activity of the present disclosure can function as a promoter is not particularly limited, specifically. microorganisms belonging to the genus Corynebacterium or the genus Escherichia may be exemplified, more specifically, Corynebacterium glutamicum, Corynebacterium ammoniagenes, Escherichia coli K12, etc., and even more specifically, Corynebacterium glutamicum or Escherichia coli, but is not limited thereto and any microorganism belonging to the genus Corynebacterium or the genus Escherichia may be included without limitation.

Still another aspect of the present disclosure provides an expression cassette for a target protein which includes the nucleic acid molecule having a promoter activity and a gene encoding the target protein.

The nucleic acid molecule is the same as explained above.

As used herein, the term "expression cassette" refers to a unit cassette which includes a promoter and a gene encoding a target protein, which is operably linked downstream of the promoter, to be capable of expressing the target protein for its production. Various factors that can aid the efficient production of the target protein may be included inside or outside of the expression cassette.

Conventionally, the expression cassette may include a promoter operably linked to the polynucleotide, a transcription termination signal, a ribosome-binding domain, and a translation termination signal.

Specifically, the expression cassette may be in a form where the gene encoding the target protein is operably linked downstream of the promoter.

As used herein, the term "expression cassette" refers to a protein which is desired to be expressed from a microorganism. Specifically, any protein that is to be expressed from the microorganism may be included without limitation (e.g., a protein encoded by an ATPE gene), but is not limited thereto.

The protein encoded by ATPE gene, i.e., a psicose epimerase, refers to a psicose-3-epimerase which has an activity of converting fructose into psicose. The sequence of the ATPE gene can be easily obtained by one of ordinary skill in the art from a known database such as GenBank of the NIH (U.S.). Additionally, the enzyme may include, for example, the amino acid sequence of SEQ ID NO: 1 of Korean Patent Application Publication No. 10-2011-0035805 or a functional fragment thereof, but is not limited thereto. As used herein, the term "functional fragment" includes a modification in an amino acid sequence by substitution, insertion, or deletion, etc., in part of the amino acid sequence and it is not particularly limited as long as the fragment has an activity of converting fructose into psicose.

The ATPE gene is one of the target genes that can be operably linked to a nucleic acid molecule having a promoter activity of the present disclosure and is only an illustrative embodiment. Any protein that can be expressed in a recombinant microorganism may be used as a target protein without limitation.

As used herein, the term "operably linked" refers to a functional linkage between a gene sequence and a promoter sequence so that the nucleic acid sequence having a promoter activity of the present disclosure can initiate and mediate the transcription of the gene encoding the target protein. The operable linkage may be prepared using a genetic recombination technology known in the art, and the site-specific DNA cleavage and linkage may be prepared using enzymes, etc., for cleavage and linkage in the art, but is not limited thereto.

Still another aspect of the present disclosure provides a recombinant vector which includes a nucleic acid molecule having the promoter activity.

The nucleic acid molecule is the same as explained above.

The recombinant vector may further include a gene encoding a target protein. That is, the recombinant vector may include an expression cassette for the target protein. The gene may be in a form operably linked to the nucleic acid molecule having the promoter activity within the vector.

As used herein, the term "vector" refers to an artificial DNA molecule possessing a genetic material to be capable of expressing a target gene in an appropriate host, and specifically refers to a DNA construct including the nucleotide sequence of a gene operably linked to an appropriate control sequence. The control sequence may include a promoter capable of initiating transcription, any operator sequence capable of controlling such transcription, a sequence encoding an appropriate mRNA ribosome-binding domain, and a sequence for controlling the termination of transcription and translation, but is not limited thereto. For the purpose of the present disclosure, the promoter may be spl1 promoter of the present disclosure.

The recombinant vector used in the present disclosure may not be particularly limited as long as the vector is replicable in the host cell, and any vector known in the art may be used. Examples of the vector conventionally used may include natural or recombinant plasmids, cosmids, viruses, and bacteriophages. The vectors to be used in the present disclosure are not particularly limited but any expression vector known in the art may be used. For example, as a phage vector or cosmid vector, pWE15, M13, MBL3, MBL4, IXII, ASHII, APII, t10, t11, Charon4A, Charon21A, etc., may be used; and as a plasmid vector, those based on pBR, pUC, pBluescriptII, pGEM, pTZ, pCL, pET, etc., may be used. The vectors that can be used in the present disclosure are not particularly limited but any known expression vector may be used. For example, pECCG117, pDZ, pACYC177, pACYC184, pCL, pUC119, pBR322, pMW118, pCC1BAC, pCES208, pXMJ19 vectors, etc., may be used, but the vectors are not limited thereto.

Additionally, the endogenous promoter in a chromosome may be replaced with the nucleic acid molecule having a promoter activity of the present disclosure through a vector for inserting into a host cell. The insertion of the nucleic acid molecule into the chromosome may be performed using any method known in the art, e.g., by homologous recombination. Since the vector of the present disclosure can be inserted into the chromosome by homologous recombination, a selection marker for confirming the insertion of the vector into the chromosome may be further included. The selection marker is used for selection of a transformed cell. i.e., in order to confirm whether the target nucleic acid molecule has been inserted, and markers capable of providing selectable phenotypes such as drug resistance, nutrient requirement, resistance to cytotoxic agents, and expression of surface proteins may be used. Under the circumstances where selective agents are treated, only the cells capable of expressing the selection markers can survive or express other phenotypic traits, and thus the transformed cells can be easily selected.

Accordingly, even in a case of a vector where the target gene is not operably linked to the nucleic acid molecule with a promoter activity having the nucleotide sequence of SEQ ID NO: 1 of the present disclosure, the endogenous promoter in a host cell (e.g., a microorganism of the genus *Corynebacterium*) may be replaced with the nucleic acid molecule by homologous recombination. By doing so, an endogenous gene of a host cell (e.g., a microorganism of the genus *Corynebacterium*) may be overexpressed.

In the recombinant vector, the gene encoding the target protein may be an ATPE gene, but is not limited thereto. In this case, the recombinant vector may be an ATPE gene which is operably linked to the nucleic acid molecule with a promoter activity having the nucleotide sequence of SEQ ID NO: 1, for example, "pFIS-2-ATPE" or "pFIS-2-ATPE-2" used in an exemplary embodiment of the present disclosure, but is not limited thereto.

Still another aspect of the present disclosure provides a recombinant microorganism introduced with the above vector.

The vector is the same as explained above.

The vector may be a vector which contains a nucleic acid molecule having a promoter activity or a vector which contains the nucleic acid molecule having a promoter activity and a gene encoding a target protein.

The vector may be introduced into a microorganism by transformation.

As used herein, the term "transformation" refers to a process of introducing a vector which includes the promoter according to the present disclosure, or additionally includes a gene encoding a target protein, into a host cell. For the transformed gene encoding a target protein, it does not matter whether the gene is inserted into the chromosome of a host cell and located thereon or located outside of the chromosome, as long as the gene can be expressed in the host cell.

The method of transforming a vector of the present disclosure may include any method which can introduce nucleic acids into a cell, and the transformation may be performed by selecting an appropriate technique as known in the art according to the host cell. For example, the method may include electroporation, calcium phosphate ($CaPO_4$) precipitation, calcium chloride ($CaCl_2$) precipitation, microinjection, a polyethylene glycol (PEG) method, a DEAE-dextran method, a cationic liposome method, and a lithium acetate/DMSO method, etc., but is not limited thereto.

The microorganism to be used in the present disclosure may be any microorganism without limitation as long as the nucleic acid molecule having a promoter activity of the present disclosure is introduced into the microorganism and is able to operate as a promoter. Specifically, the microorganism may be one that belongs to the genus *Corynebacterium*, for example, *Corynebacterium glutamicum* or *Corynebacterium ammoniagenes*, but is not limited thereto. Additionally, the microorganism may be one that belongs to the genus *Escherichia*, for example, *Escherichia coli*, but is not limited thereto.

Still another aspect of the present disclosure provides a method for producing a target protein, which includes (a) culturing the recombinant microorganism in a medium to produce a target protein; and (b) recovering the produced target protein from the cultured microorganism or the medium.

As used herein, the term "culturing" refers to growing of a microorganism in an appropriately adjusted environment. In the present disclosure, the method of producing a target protein using a recombinant microorganism may be performed by a method well-known in the art. Specifically, the culturing may be performed continuously in a batch process, a fed batch, or a repeated fed batch process, but is not limited thereto.

The media used for culturing must meet the requirements of a particular strain in an appropriate method. The culture media for the strain belonging to the genus *Corynebacterium* or the strain belonging to the genus *Escherichia* are already known (e.g., Manual of Methods for General Bacteriology. *American Society for Bacteriology*. Washington D.C., USA, 1981). Examples of the carbon sources may include sugars and carbohydrates such as glucose, sucrose, lactose, fructose, maltose, starch, cellulose, etc.; oils and fats such as soybean oil, sunflower oil, castor oil, coconut oil, etc.; fatty acids such as palmitic acid, stearic acid, linoleic acid, etc.; alcohols such as glycerol and ethanol; and organic acids such as gluconic acid, acetic acid, and pyruvic acid, but are not limited thereto. These carbon sources may be used alone or in combination. Examples of the nitrogen sources may include peptone, yeast extract, meat gravy, malt extract, corn steep liquor (CSL), soybean flour, and urea; or inorganic nitrogen sources such as ammonium sulfate, ammonium chloride, ammonium phosphate, ammonium carbonate, and ammonium nitrate, but are not limited thereto. These nitrogen sources may also be used alone or in combination. Examples of phosphorus sources to be used may include potassium dihydrogen phosphate, dipotassium hydrogen phosphate, and corresponding sodium-containing salts, but are not limited thereto. Additionally, metal salts such as magnesium sulfate or iron sulfate may be contained in the medium. Lastly, essential materials for growth such as amino acids and vitamins may be used. Additionally, appropriate precursors may also be contained in the medium. The above source materials may be added to a medium in a batch type or continuous type by an appropriate method. These various culture methods are disclosed in references, e.g., "Biochemical Engineering" by James M. Lee, Prentice-Hall International Editions, pp 138 to 176.

The pH of the culture may be adjusted by appropriately using a basic compound such as sodium hydroxide, potassium hydroxide, and ammonia, or an acidic compound such as phosphoric acid and sulfuric acid. Additionally, an anti-foaming agent such as fatty acid polyglycol ester may be added to prevent foam generation. In order to maintain the aerobic state of the culture, oxygen or an oxygen-containing gas (e.g., air) may be injected into the culture. The culture temperature may generally be from 20° C. to 45° C., and preferably, from 25° C. to 40° C., and the temperature may vary according to conditions, but is not limited thereto.

The method for preparing a target protein of the present disclosure may include recovering a target protein from a microorganism or culture thereof. As a method for recovering a target protein from a microorganism, those methods well-known in the art, e.g., filtration, anion exchange chromatography, crystallization, HPLC, etc., may be used, but the methods are not limited thereto.

The recovering may include a purification step and one of ordinary skill in the art can select a purification step from various purification processes and use as needed.

Still another aspect of the present disclosure provides a method for producing psicose, which includes (a) culturing a microorganism where a vector including a promoter having the nucleotide sequence of SEQ ID NO: 1 and an ATPE gene is introduced; and (b) reacting the cultured microorganism with fructose to produce psicose.

The promoter, ATPE gene, vector, and microorganism are the same as explained above.

The above production method can significantly improve psicose productivity compared to any conventional case where the ATPE gene was operably linked to a known promoter and expressed in a microorganism.

DETAILED DESCRIPTION OF THE INVENTION

Hereinafter, the present disclosure will be described in more detail with reference to the following Examples, etc., to help the understanding of the present disclosure. However, these Examples can be modified in various other forms and the scope of the present disclosure should not be interpreted to be limited by these Examples. The Examples of the present disclosure are provided for the purpose of a more complete explanation to those who have average knowledge in the art.

For the synthesis of a promoter capable of inducing the expression of a target gene, a promoter having the nucleotide sequence of SEQ ID NO: 1 was synthesized by analyzing various promoter sequences derived from microorganisms of the genus *Corynebacterium* and the genus *Escherichia*, and the promoter was named as spl1 promoter (hereinafter, "Pspl1"). To measure the expression-inducing activity of Pspl1, a recombinant vector was constructed by operatively linking Pspl1 with a GFP gene or ATPE gene. The vector was transformed into a microorganism of the genus *Corynebacterium* and a transformed strain was prepared therefrom.

EXAMPLE 1

Preparation of Promoter Library

A library was prepared to screen for strong synthetic promoters which are capable of expressing high expression levels of foreign proteins in a strain of the genus *Corynebacterium*. Specifically, a library of promoters capable of exhibiting stronger expression or a different expression profile through DNA shuffling technique was obtained using the respective genomic DNA of *Corynebacterium glutamicum, Corynebacterium ammoniagenes*, and *Escherichia coli* K12.

More specifically, the genomic DNAs of *Corynebacterium glutamicum. Corynebacterium ammoniagenes*, and *Escherichia coli* K12 were first digested with DNase I into several fragments and then subjected to PCR without using primers. Accordingly, each fragment that has a similar nucleotide sequence can act as a primer for each other and a library can be prepared therefrom. The library was then introduced into a pUC19 vector by a blunt-end ligation. Then, PCR was performed using the primers of SEQ ID NO: 2 and SEQ ID NO: 3 containing a KpnI/PstI restriction site to prepare a variously synthesized promoter library.

The empty vector of the library used was pECCG117 (Korean Patent No. 10-0620092, KFCC-10673/KFCC-10674), which is a shuttle vector that can express in the strains of *Corynebacterium* and *Escherichia*. First, the gene fragment encoding the green fluorescent protein was prepared by PCR using a pGFPuv vector (Clontech Laboratories Inc., U.S.A.) as the template along with a forward primer (SEQ ID NO: 4) containing a PstI/XbaI restriction site (SEQ ID NO: 4) and a reverse primer containing the PstI/XbaI restriction site (SEQ ID NO: 5). The PCR was performed by initial denaturation at 94° C. for 5 minutes; 30 cycles consisting of denaturation at 94° C. for 30 seconds, annealing at 55° C. for 30 seconds, and polymerization at 72° C. for 1 minute; and finally amplifying at 72° C. for 7 minutes. As a result, a PCR product (SEQ ID NO: 6) containing the open reading frame (ORF) of GFP gene was obtained. The PCR product and the pECCG117, which is an empty vector, were respectively treated with restriction enzymes (PstI and XbaI), operably ligated together using a DNA ligase, and a pECCG117-gfp plasmid, which is a recombinant vector linked to GFP, was finally prepared.

The thus-obtained promoter library and the vector, into which the green fluorescence protein (hereinafter, GFP) was cloned, were treated with restriction enzymes (KpnI and PstI) and ligated using a DNA ligase to prepare a promoter library plasmid.

The thus-prepared plasmid was transformed into *Corynebacterium glutamicum* ATCC13032 to prepare a synthetic promoter library.

The thus-prepared synthetic promoter library of *Corynebacterium glutamicum* was screened in cells which show fluorescence by expressing GFP after undergoing steps of culturing, obtaining the microorganism cells, and pretreatment. After several rounds of screening, the final strong synthetic promoter Psl1 was obtained and the promoter had the nucleotide sequence of SEQ ID NO: 1.

EXAMPLE 2

Confirmation of Expression-inducing Activity in *Corynebacterium glutamicum* by Comparison of Activity Between the Promoter Finally Obtained Through Screening and Other Promoters The activity of promoters according to the expression of GFP, which is a reporter protein, was analyzed using the pECCG117-Pspl1-gfp plasmid having the Pspl1 promoter finally obtained in Example 1, the pECCG117-Pcj4-gfp plasmid having the conventionally-known Pcj4 promoter (Korean Patent No. 10-0620092) as a positive control group, and the pECCG117 plasmid as a negative control group.

Specifically, for the confirmation of the activity of Pspl1, the transformed strain of *Corynebacterium glutamicum* ATCC13032/pECCG117, *Corynebacterium glutamicum* ATCC13032/pECCG177-Pcj4-gfp, and *Corynebacterium glutamicum* ATCC13032/pECCG117-Pspl1-gfp obtained above were cultured as described below, and their GFP activity was measured.

Each of the transformed strain of *Corynebacterium glutamicum* was inoculated in a 1:20 ratio into a 250 mL corner-baffle flask containing 25 mL of a medium (glucose (20 g), ammonium sulfate (5 g), yeast extract (5 g), urea (1.5 g), $KH_2PO_4$ (4 g), $K_2HPO_4$ (8 g), $MgSO_4 \cdot 7H_2O$ (0.5 g), biotin (150 μg), thiamine HCl (1.5 mg), calcium-pantothenic acid (3 mg), and nicotinamide (3 mg) (based on 1 L of distilled water), pH 7.2), respectively, and cultured in a shaking incubator (200 rpm) at 30° C. until the absorbance at 600 nm reached 10.0. The microorganism cells were recovered from the culture by centrifugation (5,000 rpm, 15 minutes), washed twice with a 0.1% Tris-HCl (pH 8.0) buffer, and suspended in the same buffer to have a turbidity of about 160. The suspension was charged with glass beads (1.25 g of glass beads/1.5 mL of suspension) and the cells were disrupted for 6 minutes using a bead beater. Then, the supernatant was recovered by centrifugation (15,000 rpm, 20 minutes), and the protein concentration was quantified by the Bradford method (Bradford, MM 1976. *Anal. Biochem.* 72: 248 to 254)

An extract of the microorganism cells in the same amount was subjected to irradiation of excitation light at 488 nm using the Laure Gory method, etc., (*FEMS Microbiology Letters* 194, 127 to 133, 2001) and the light emitted therefrom was measured using the LS-50B spectrophotometer device (Perkin-Elmer), thereby measuring the expression level of the GFP gene (Table 1).

TABLE 1

| Strain | Fluorescence Sensitivity |
| --- | --- |
| ATCC13032/pECCG117 | 0.0 |
| ATCC13032/Pcj4-gfp | 897.2 |
| ATCC13032/Pspl1-gfp | 3256.3 |

As shown in Table 1, Pspl1 actually had a promoter activity in *Corynebacterium glutamicum*, and it was confirmed that Pspl1 is an excellent promoter capable of expressing the GFP gene more strongly than existing Pcj4 promoter prepared by the applicant's company.

EXAMPLE 3

Preparation of Vector for Expression of ATPE Including Sequence of Pspl1 Promoter For the evaluation of the promoter with improved expression of *Corynebacterium* (hereinafter, Pspl1), in an exemplary embodiment, a vector for a strain of *Corynebacterium*, in which the expression of ATPE (cyclic epimerase derived from *Agrobacterium tumefaciens* ATCC 33970) was increased, was prepared.

Figure 1:
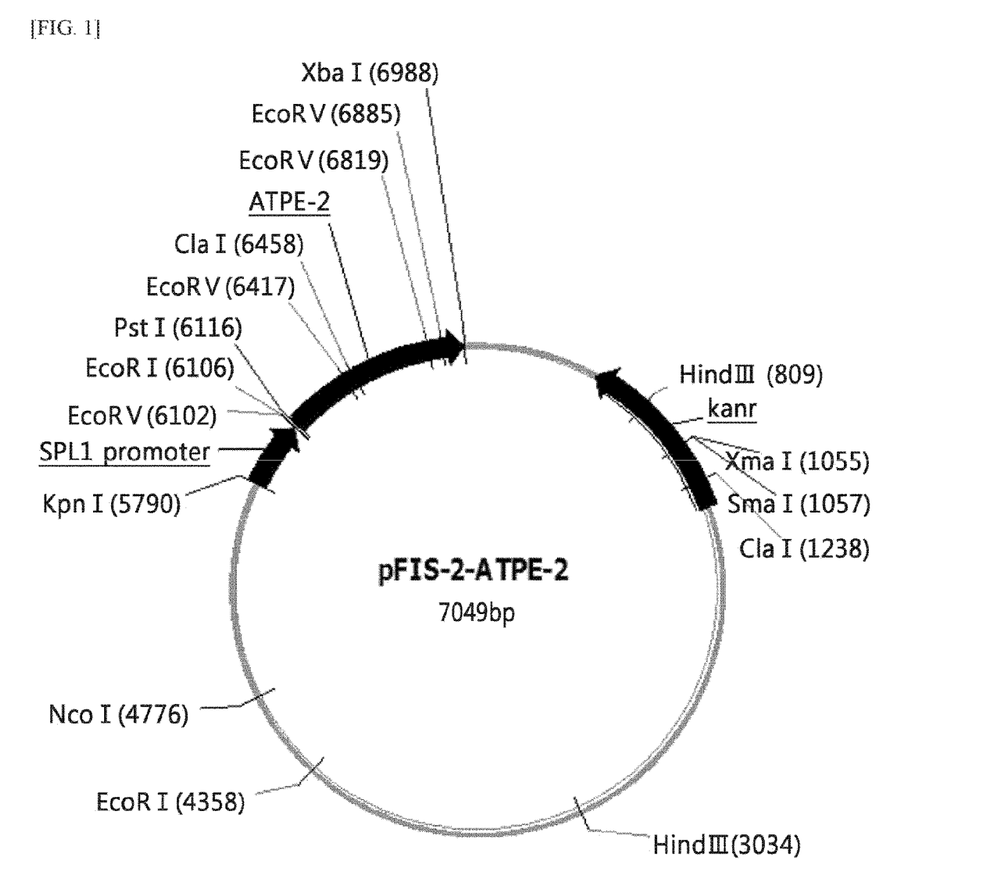
FIG. 1 shows the map of pFIS-2-ATPE-2 vector.

The open reading frame (ORF) of ATPE gene was amplified by performing PCR (30 cycles in the following conditions: 94° C. for 30 seconds, 55° C. for 30 seconds, and 72° C. for 1 minute) using the pET24-ATPE vector (the same nucleotide sequence as that of SEQ ID NO: 1 disclosed in Korean Patent Application Publication No. 10-2011-0035805) or pET24-ATPE-2 vector (the same as that of the nucleotide sequence disclosed in Korean Patent No. 10-1203856; variants with improved thermostability, I33L-S213C) along with primers having the nucleotide sequences of SEQ ID NOS: 7 and 8. The pECCG117-Pspl1-GFP vector for the strain of the genus *Corynebacterium* prepared in Example 1 was treated with restriction enzymes (PstI and XbaI), and then the ORF fragments of ATPE gene and ATPE-2 (variants with improved ATPE stability) were operably ligated using the BD In-Fusion kit, and thereby the pECCG117-Pspl1-ATPE vector (hereinafter, "pFIS-2-ATPE") and the pECCG117-Pspl1-ATPE-2 (hereinafter, "pFIS-2-ATPE-2") for the strain of the genus *Corynebacterium* were finally prepared (FIG. 1).

EXAMPLE 4

Confirmation of Expression of Psicose-producing Enzyme and Activity Thereof in *Corynebacterium glutamicum* Strain The "pFIS-2-ATPE" and "pFIS-2-ATPE-2" vectors prepared above were introduced into the ATCC13032 strain by electroporation to prepare FIS-2-ATPE and FIS-2-ATPE-2 strains. Of these, the FIS-2-ATPE-2 strain was deposited at Korean Culture Center of Microorganisms (KCCM) on Mar. 27, 2015, and assigned Accession No. KCCM 11678P. The strains were cultured in an Erlenmeyer flask using the medium of Example 1 (glucose (20 g), ammonium sulfate (5 g), yeast extract (5 g), urea (1.5 g), $KH_2PO_4$ (4 g), $K_2HPO_4$ (8 g), $MgSO_4 \cdot 7H_2O$ (0.5 g), biotin (150 μg), thiamine HCl (1.5 mg), calcium-pantothenic acid (3 mg), and nicotinamide (3 mg) (based on 1 L of distilled water), pH 7.2) and the activity of ATPE was measured.

Figure 2:
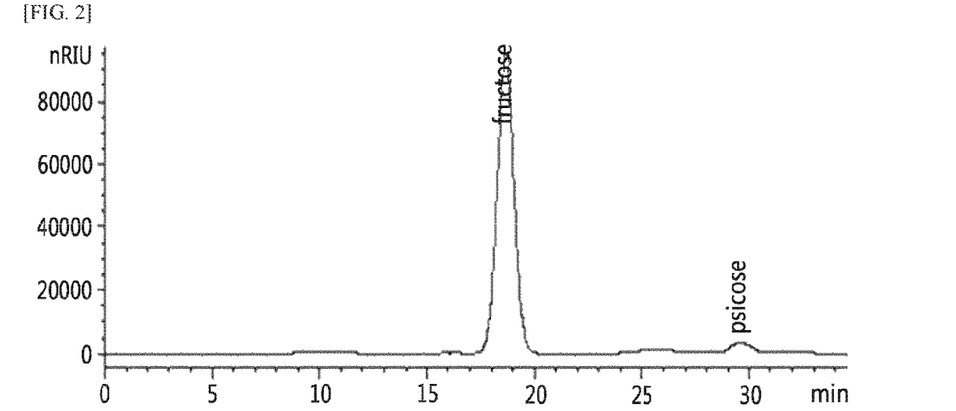
FIG. 2 shows HPLC chromatography after reacting *Corynebacterium glutamicum* ATCC13032/pECCG117-Pcj4-ATPE (FIS-4-ATPE) with a fructose substrate.
Figure 3:
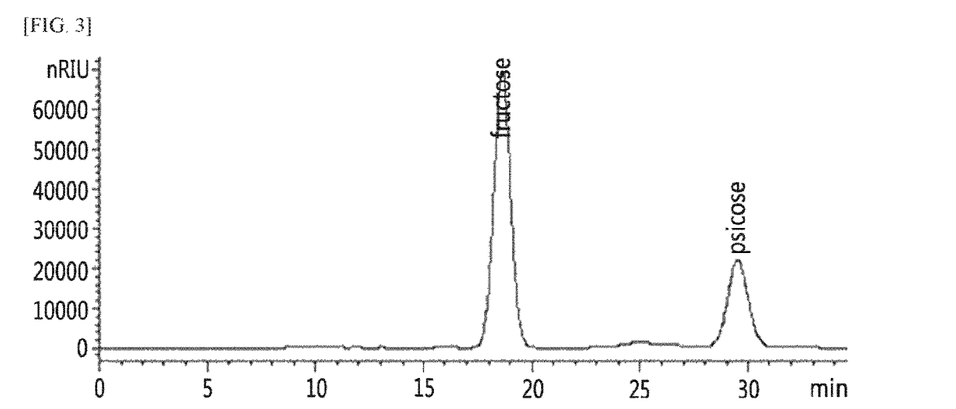
FIG. 3 shows HPLC chromatography after reacting *Corynebacterium glutamicum* ATCC13032/pECCG117-Pcj4-ATPE (FIS-4-ATPE) with a fructose substrate.
Figure 4:
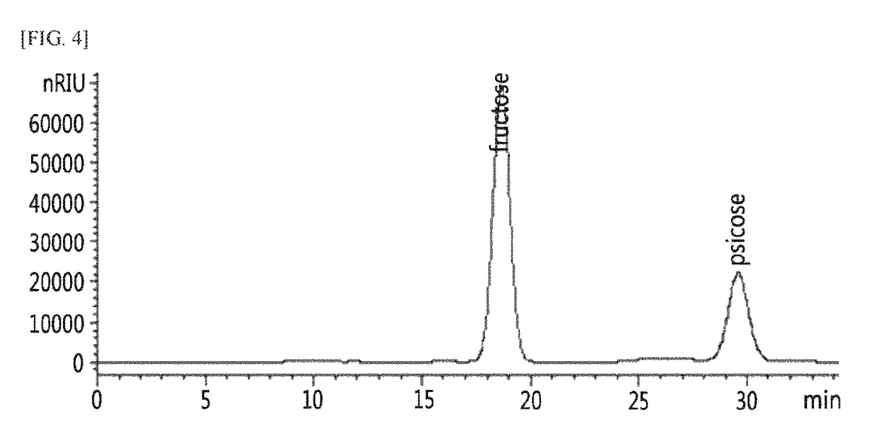
FIG. 4 shows HPLC chromatography after reacting ATCC13032/pECCG117-Pspl1-ATPE-2 (FIS-2-ATPE-2) with a fructose substrate.

Each of the strains cultured overnight in LB solid medium kept in a 30° C. incubator was inoculated into 25 mL of a medium and cultured in the incubator (30° C., 200 rpm) for 24 hours. After the cultivation, the resulting supernatant was removed by centrifugation and the microorganism bodies obtained therefrom were washed with cold PBS. Each of the thus-obtained pellets was dissolved in an EPPS solution (pH 8.0) to a concentration of 20% (w/v), treated with POESA (1 mg/mL) and reacted at room temperature for 1 hour, and centrifuged. Each of the pellets obtained by centrifugation was dissolved in the EPPS solution (pH 8.0) to a concentration of 20% (w/v), treated with a fructose solution (300 g/L) and reacted at 50° C. for 3 hours, and the reaction was stopped by heat treatment. Then, the supernatant was recovered by centrifugation and the amount of psicose production was measured by HPLC analysis (FIGS. 2 to 4).

TABLE 2

| Strains | Fructose (g/L) | Psicose (g/L) |
| --- | --- | --- |
| ATCC13032/pECCG117 | 300 | 0 |
| ATCC13032/pECCG117-Pcj4-ATPE | 285.86 | 11.06 |
| ATCC13032/pECCG117-Pspl1-ATPE (FIS-2-ATPE) | 224.15 | 71.57 |
| ATCC13032/pECCG117-Pspl1-ATPE-2 (FIS-2-ATPE-2) | 223.86 | 73.55 |

As shown in Table 2 above, it was confirmed that, among the *Corynebacterium* strains. ATPE gene was expressed, derived from wild-type strains prepared above, *Corynebacterium glutamicum* ATCC13032/pECCG117-Pspl1-ATPE (FIS-2-4 TPE) and *Corynebacterium glutamicum*

ATCC13032/pECCG117-Pspl1-ATPE-2 (FIS-2-ATPE-2) showed a significant increase in psicose production compared to that of *Corynebacterium glutamicum* ATCC13032/pECCG117-Pcj4-ATPE (FIS-4-ATPE).

Summarizing the above, since the Pspl1 promoter of the present disclosure can significantly increase the expression of a target gene in a recombinant microorganism compared to the conventionally known promoters, it can be effectively used in various industrial fields where high-yield production of functional materials is required.

From the foregoing, a skilled person in the art to which the present disclosure pertains will be able to understand that the present disclosure may be embodied in other specific forms without modifying the technical concepts or essential characteristics of the present disclosure. In this regard, the exemplary embodiments disclosed herein are only for illustrative purposes and should not be construed as limiting the scope of the present disclosure. On the contrary, the present disclosure is intended to cover not only the exemplary embodiments but also various alternatives, modifications, equivalents, and other embodiments that may be included within the spirit and scope of the present disclosure as defined by the appended claims.

The invention claimed is:

1. An isolated nucleic acid molecule having a promoter activity, wherein the isolated nucleic acid molecule comprises the nucleotide sequence of SEQ ID NO: 1.

2. A target protein expression cassette comprising the isolated nucleic acid molecule having a promoter activity of claim 1 and a gene encoding a target protein.

3. A recombinant vector comprising the isolated nucleic acid molecule of claim 1 or the target protein expression cassette of claim 2.

4. The recombinant vector of claim 3, wherein the target protein is a psicose-3-epimeras.

5. A method for producing psicose, comprising:
   (a) culturing the microorganism introduced with the vector of claim 4; and
   (b) reacting the cultured microorganism with fructose to produce psicose.

6. A recombinant microorganism introduced with the vector of claim 4.

7. The recombinant microorganism of claim 6, wherein the microorganism is a microorganism of the genus *Corynebacterium*.

8. The recombinant microorganism of claim 7, wherein the microorganism of the genus *Corynebacterium* is *Corynebacterium glutamicum* or *Corynebacterium ammoniagenes*.

9. The recombinant microorganism of claim 6, wherein the microorganism is a microorganism of the genus *Escherichia*.

10. The recombinant microorganism of claim 9, wherein the microorganism of the genus *Escherichia* is *Escherichia coli*.

11. A method for producing a target protein, comprising:
    (a) culturing the recombinant microorganism of claim 6 in a medium to produce a target protein; and
    (b) recovering the produced target protein from the cultured microorganism or the medium.

12. A recombinant microorganism introduced with the vector of claim 3.

13. The recombinant microorganism of claim 12, wherein the microorganism is a microorganism of the genus *Corynebacterium*.

14. The recombinant microorganism of claim 13, wherein the microorganism of the genus *Corynebacterium* is *Corynebacterium glutamicum* or *Corynebacterium ammoniagenes*.

15. The recombinant microorganism of claim 12, wherein the microorganism is a microorganism of the genus *Escherichia*.

16. The recombinant microorganism of claim 15, wherein the microorganism of the genus *Escherichia* is *Escherichia coli*.

17. A method for producing a target protein, comprising:
    (a) culturing the recombinant microorganism of claim 12 in a medium to produce the target protein; and
    (b) recovering the produced target protein from the cultured microorganism or the medium.

* * * * *

SEQUENCE LISTING

```
<160> NUMBER OF SEQ ID NOS: 8

<210> SEQ ID NO 1
<211> LENGTH: 308
<212> TYPE: DNA
<213> ORGANISM: Artificial Sequence
<220> FEATURE:
<223> OTHER INFORMATION: nucleic acid molecule having a promoter
      activity - Pspl1

<400> SEQUENCE: 1
atgctagggc gaaaagcacg gcgagcagat tgctttgcac ttgattcagg gtagttgact     60
aaagagttgc tcgcgaagta gcacctgtca cttttgtctc aaatattaga tcttatccgg    120
attagatcta gcgacaagta cattctctaa aatcgagcgt tttaacgctc ctagggctgg    180
tttgcctgaa ggaattttcg accgatttaa aacctgtaag ttcaataatc gtgaattttg    240
gcagcaacag ttaaatgggg tacaatggaa acgtgcaaaa gcatagatta ttggaggaga    300
tcaaaaca                                                             308

<210> SEQ ID NO 2
<211> LENGTH: 33
<212> TYPE: DNA
<213> ORGANISM: Artificial Sequence
<220> FEATURE:
<223> OTHER INFORMATION: Primer 1
<220> FEATURE:
<221> NAME/KEY: misc_feature
<222> LOCATION: (1)...(33)
<223> OTHER INFORMATION: n = A,T,C or G

<400> SEQUENCE: 2
gaattcgagc tcggtaccat gnnnnnnnnn nnn                                  33

<210> SEQ ID NO 3
<211> LENGTH: 31
<212> TYPE: DNA
<213> ORGANISM: Artificial Sequence
<220> FEATURE:
<223> OTHER INFORMATION: Primer 2
<220> FEATURE:
<221> NAME/KEY: misc_feature
<222> LOCATION: (1)...(31)
<223> OTHER INFORMATION: n = A,T,C or G

<400> SEQUENCE: 3
caagcttgca tgcctgcagn nnnnnnnnn n                                     31

<210> SEQ ID NO 4
<211> LENGTH: 23
<212> TYPE: DNA
<213> ORGANISM: Artificial Sequence
<220> FEATURE:
```

<223> OTHER INFORMATION: Primer 3

<400> SEQUENCE: 4
tctagaatga gtaaaggaga aga                                                 23

<210> SEQ ID NO 5
<211> LENGTH: 23
<212> TYPE: DNA
<213> ORGANISM: Artificial Sequence
<220> FEATURE:
<223> OTHER INFORMATION: Primer 4

<400> SEQUENCE: 5
ctgcagttat ttgtagagct cat                                                 23

<210> SEQ ID NO 6
<211> LENGTH: 717
<212> TYPE: DNA
<213> ORGANISM: Artificial Sequence
<220> FEATURE:
<223> OTHER INFORMATION: Synthetic PCR product containing the open
      reading frame (ORF) of GFP gene

<400> SEQUENCE: 6
atgagtaaag gagaagaact tttcactgga gttgtcccaa ttcttgttga attagatggt         60
gatgttaatg ggcacaaatt ttctgtcagt ggagagggtg aaggtgatgc aacatacgga        120
aaacttaccc ttaaatttat ttgcactact ggaaaactac ctgttccatg gccaacactt        180
gtcactactt tctcttatgg tgttcaatgc ttttcccgtt atccggatca tatgaaacgg        240
catgactttt tcaagagtgc catgcccgaa ggttatgtac aggaacgcac tatatctttc        300
aaagatgacg ggaactacaa gacgcgtgct gaagtcaagt ttgaaggtga taccttgtt         360 aatcgtatcg agttaaaagg tattgatttt aagaagatg gaaacattct cggacacaaa         420
ctcgagtaca actataactc acacaatgta tacatcacgg cagacaaaca aaagaatgga        480
atcaaagcta acttcaaaat tcgccacaac attgaagatg gatccgttca actagcagac        540
cattatcaac aaaatactcc aattggcgat ggccctgtcc ttttaccaga caaccattac        600
ctgtcgacac aatctgccct ttcgaaagat cccaacgaaa agcgtgacca catggtcctt        660
cttgagtttg taactgctgc tgggattaca catggcatgg atgagctcta caaataa          717

<210> SEQ ID NO 7
<211> LENGTH: 42
<212> TYPE: DNA
<213> ORGANISM: Artificial Sequence
<220> FEATURE:
<223> OTHER INFORMATION: Primer 5

<400> SEQUENCE: 7
atctaggaga ttaactgcag atgaaacacg gcatctatta tt                           42

<210> SEQ ID NO 8
<211> LENGTH: 36
<212> TYPE: DNA
<213> ORGANISM: Artificial Sequence
<220> FEATURE:
<223> OTHER INFORMATION: Primer 6

<400> SEQUENCE: 8
gtggatcccc cgggtctaga tcagccacca agaacg                                  36